United States Patent
Masson et al.

(10) Patent No.: US 11,395,921 B2
(45) Date of Patent: Jul. 26, 2022

(54) INTRAVASCULAR ELECTRODE ARRAYS FOR NEUROMODULATION

(71) Applicant: Interventional Autonomics Corporation, Chapel Hill, NC (US)

(72) Inventors: Stephen C. Masson, Raleigh, NC (US); Jeffrey A Smith, Petaluma, CA (US)

(73) Assignee: NuXcel2 LLC, Brooklyn Park, MN (US)

( * ) Notice: Subject to any disclaimer, the term of this patent is extended or adjusted under 35 U.S.C. 154(b) by 374 days.

(21) Appl. No.: 16/536,285

(22) Filed: Aug. 8, 2019

(65) Prior Publication Data

US 2019/0374778 A1 Dec. 12, 2019

Related U.S. Application Data

(63) Continuation of application No. 16/536,274, filed on Aug. 8, 2019, now abandoned, which is a continuation of application No. 15/237,894, filed on Aug. 16, 2016, now abandoned, which is a continuation of application No. 14/516,734, filed on Oct. 17, 2014, now Pat. No. 9,446,240, which is a continuation of application No. 13/547,031, filed on Jul. 11, 2012, now Pat. No. 9,067,071.

(60) Provisional application No. 61/639,982, filed on Apr. 29, 2012.

(51) Int. Cl.
*A61N 1/36* (2006.01)
*A61N 1/05* (2006.01)

(52) U.S. Cl.
CPC .......... *A61N 1/36117* (2013.01); *A61N 1/056* (2013.01); *A61N 1/0551* (2013.01); *A61N 1/36053* (2013.01); *A61N 1/36114* (2013.01); *A61N 1/36135* (2013.01); *A61N 1/36139* (2013.01)

(58) Field of Classification Search
CPC . A61N 1/056; A61N 1/36053; A61N 1/36114
See application file for complete search history.

(56) References Cited

U.S. PATENT DOCUMENTS

| | | | | |
|---|---|---|---|---|
| 7,813,812 B2* | 10/2010 | Kieval | ............... | A61B 5/02028 607/118 |
| 7,949,409 B2* | 5/2011 | Bly | ........................ | A61N 1/057 607/116 |
| 2005/0288730 A1 | 12/2005 | Deem et al. | | |

(Continued)

OTHER PUBLICATIONS

Wikipedia, "Face (geometry)." https://en.wikipedia.org/wiki/Face_(geometry), accessed Mar. 2, 2022. (Year: 2022).*

(Continued)

*Primary Examiner* — Michael W Kahelin

(57) ABSTRACT

A neuromodulation catheter is positionable in a blood vessel having a wall for use in delivering therapeutic energy to targets external to the blood vessel. An electrically insulative substrate such as an elongate finger is carried at a distal end of the catheter body. The substrate has a first face carrying a plurality of electrodes, and a second face on an opposite side of the substrate from the first face. The finger is biased such that when expanded within the blood vessel, it forms a spiral configuration with the first face facing outwardly to bias the electrodes in contact with the blood vessel wall.

6 Claims, 4 Drawing Sheets

(56) References Cited

U.S. PATENT DOCUMENTS

| | | |
|---|---|---|
| 2007/0288076 A1* | 12/2007 | Bulkes ............... A61N 1/37211 607/116 |
| 2008/0004673 A1 | 1/2008 | Rossing et al. |
| 2010/0023088 A1* | 1/2010 | Stack ...................... A61N 1/05 607/44 |
| 2010/0036451 A1 | 2/2010 | Hoffer |
| 2011/0196298 A1 | 8/2011 | Anderson et al. |
| 2013/0289686 A1* | 10/2013 | Masson ................ A61N 1/0551 607/122 |

OTHER PUBLICATIONS

Search Report for PCT/US2013/038695.
Office Action for U.S. Appl. No. 13/873,082.

* cited by examiner

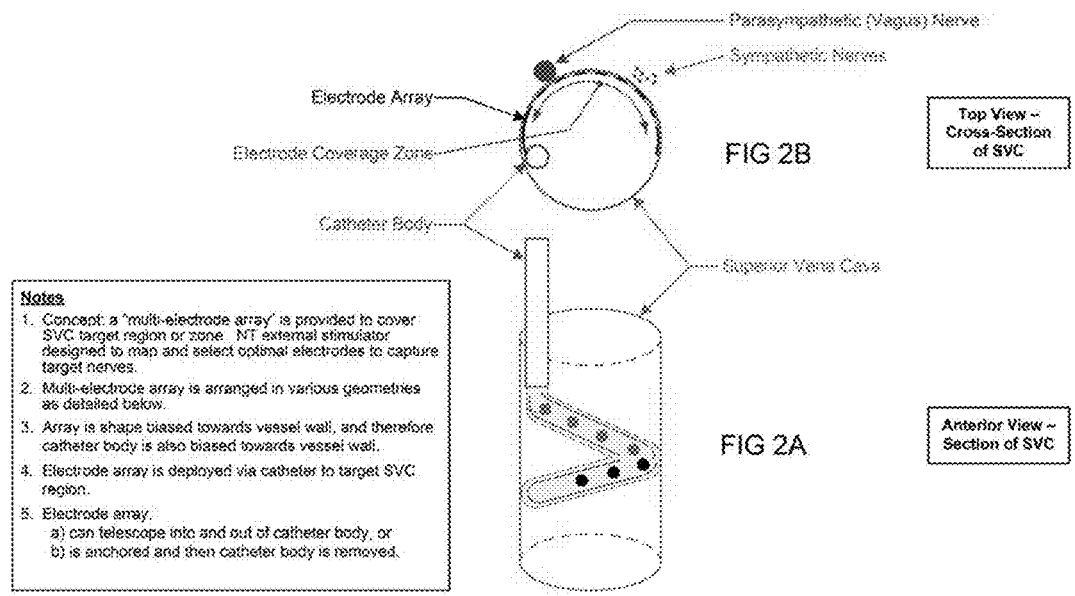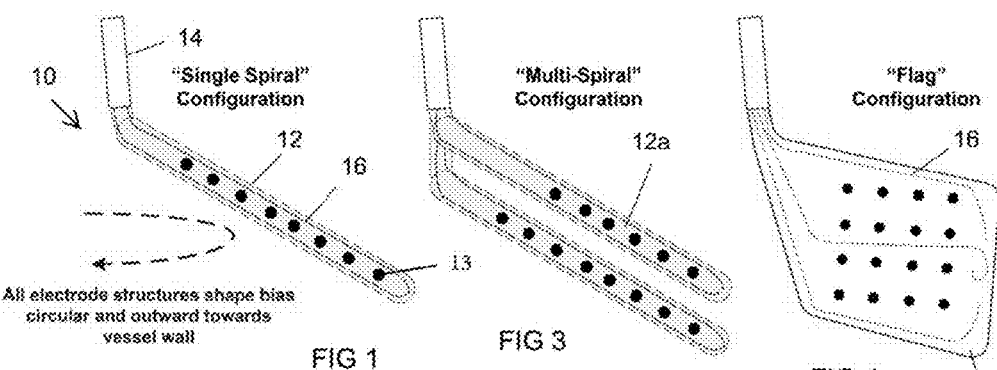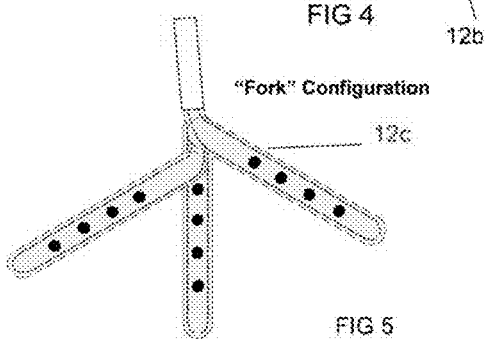

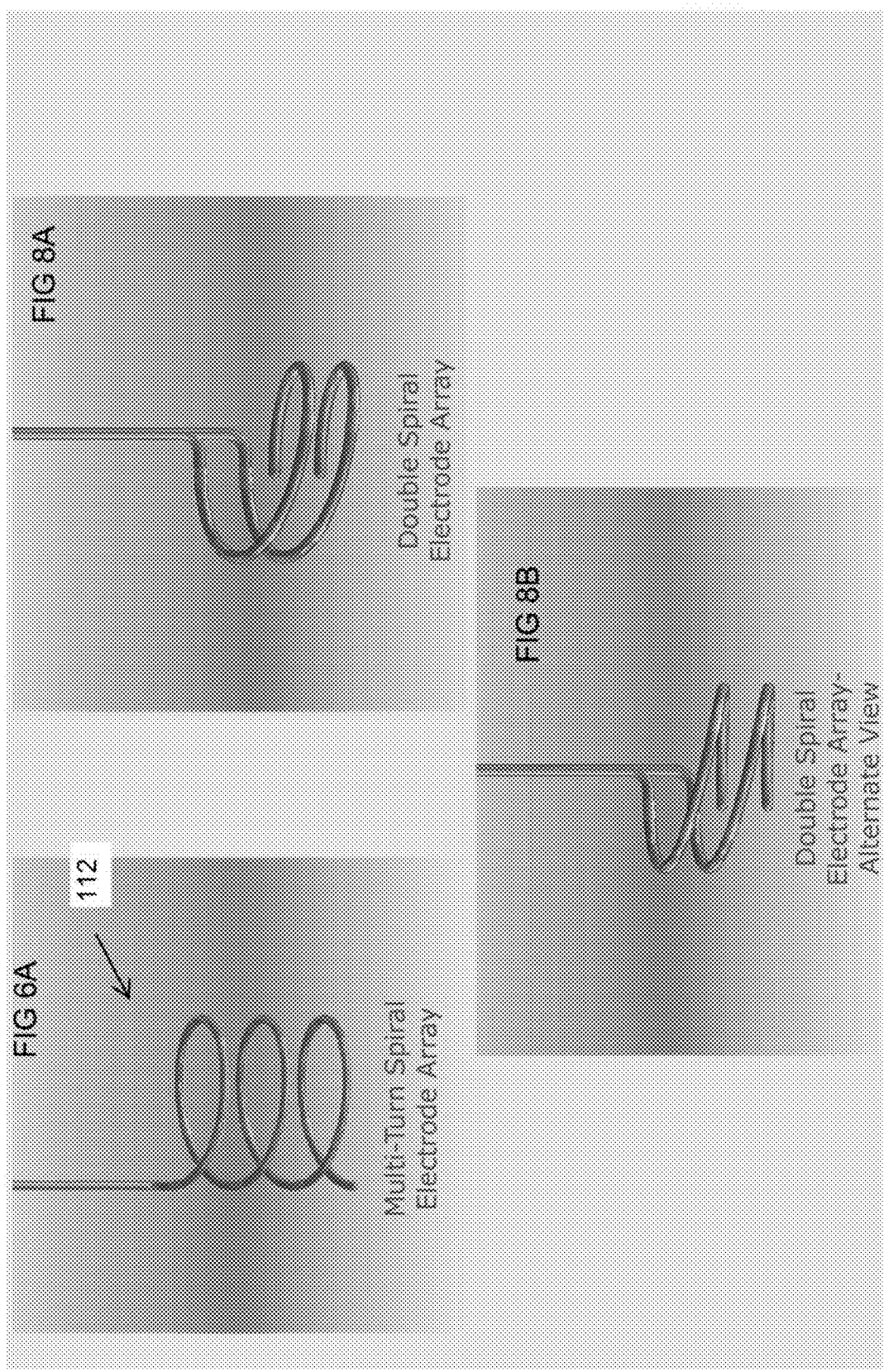

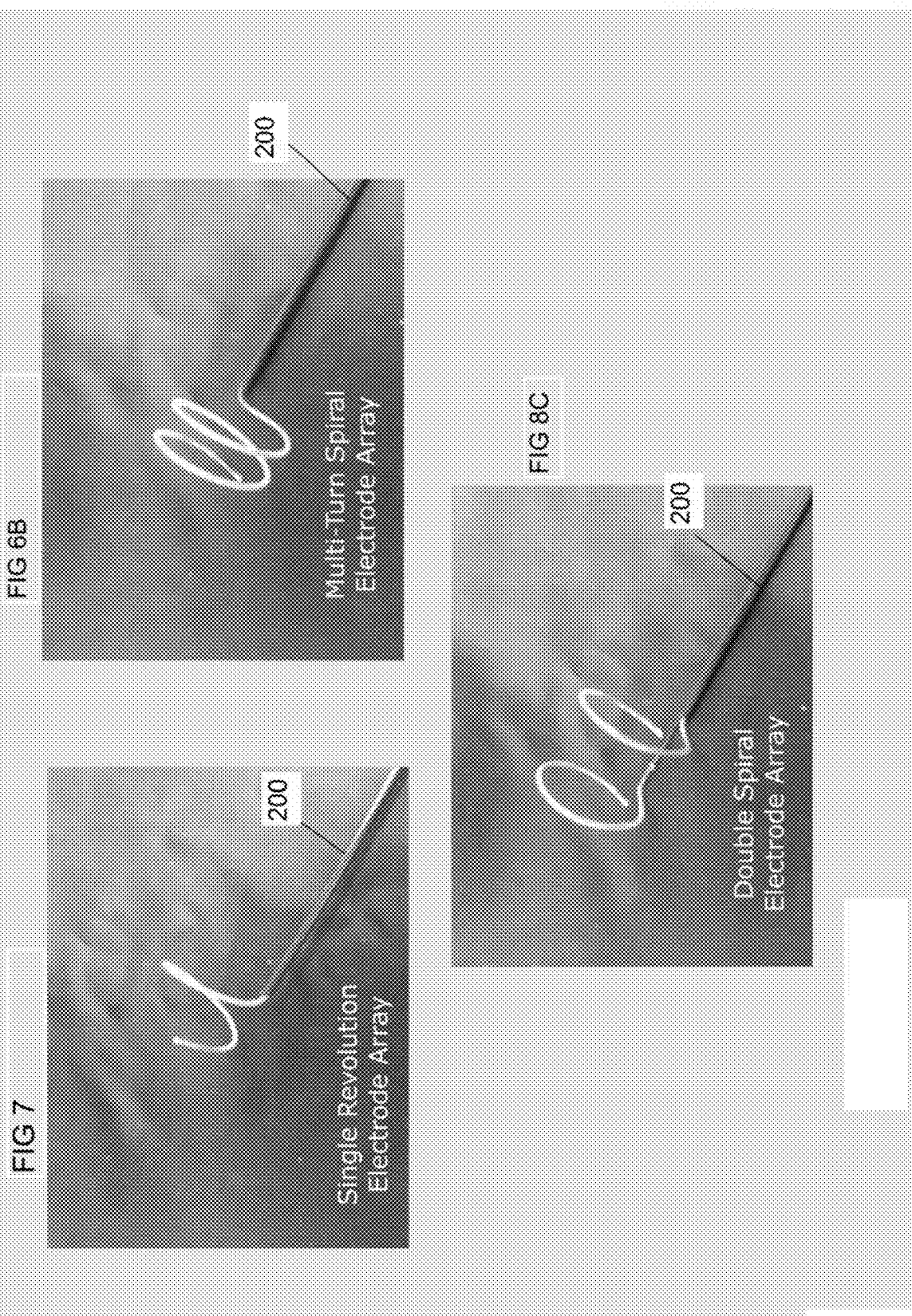

INTRAVASCULAR ELECTRODE ARRAYS FOR NEUROMODULATION

This application is a continuation of U.S. application Ser. No. 15/237,894, filed Aug. 16, 2016, which is a continuation of U.S. application Ser. No. 14/516,734, filed Oct. 17, 2014, now U.S. Pat. No. 9,446,249, which is a continuation U.S. application Ser. No. 13/547,031, U.S. Pat. No. 9,067,071, filed Jul. 11, 2012, which claims the benefit of U.S. Provisional Application No. 61/639,982, filed Apr. 29, 2012. Each of the foregoing applications is incorporated herein by reference.

TECHNICAL FIELD OF THE INVENTION

The present application generally relates to intravascular electrode arrays for use in neuromodulation. More particularly, the application relates to electrode supports used to position the intravascular electrodes against the interior wall of a blood vessel.

BACKGROUND

Prior applications filed by the owners of the present application describe methods using electrodes positioned in blood vessel. The electrodes are energized to stimulate or otherwise neuromodulate nerve fibers or other nervous system targets located outside the blood. Those applications include U.S. Publication No. 2007/0255379, entitled Intravascular Device for Neuromodulation, U.S. 2010/0023088, entitled System and Method for Transvascularly Stimulating Contents of the Carotid Sheath, U.S. application Ser. No. 13/281,399, entitled Intravascular Electrodes and Anchoring Devices for Transvascular Stimulation, International Application PCT/US12/35712, entitled Neuromodulation Systems and Methods for Treating Acute Heart Failure Syndromes, and International Application No. PCT/US2012/046329, entitled System and Method for Neuromodulation. Each of these applications is fully incorporated herein by reference.

Proper placement of intravascular electrodes is essential for neuromodulation. The electrodes must be positioned to capture the target nerve fibers, while avoiding collateral stimulation of non-target nerve fibers. Mapping procedures are typically performed at the time of electrode placement to identify the optimal electrode location. Mapping can be manually controlled by the clinician or automatically controlled by the neuromodulation system. During mapping, different electrodes, combinations of electrodes, or arrays can be independently energized while the target response to the stimulus is monitored. For stimulation relating to cardiac or hemodynamic function, parameters such as heart rate, blood pressure, ventricular inotropy and/or cardiac output might be monitored. In some cases mapping includes additional steps of repositioning the electrode carrying member so as to allow additional electrode sites to be sampled. The mapping process is performed until the optimal electrode or combination of electrodes for the desired therapy array is identified.

The present application describes electrode support configurations that may be used in chronically-implantable or acute neuromodulation systems, including, but not limited to, those described in the referenced applications.

BRIEF DESCRIPTION OF THE DRAWINGS

FIG. 1 shows a first embodiment of an electrode support. The electrode support is shown as flattened;

FIG. 2A is an anterior view of a superior vena cava showing the electrode support of FIG. 1 deployed within the superior vena cava.

FIG. 2B is a superior cross-section view of the superior vena cava, showing positioning of the electrode support of FIG. 1 in contact with the posterior surface of the interior blood vessel wall, so that its electrodes can deliver electrical therapy to a vagus nerve and sympathetic cardiac nerve fibers disposed outside the blood vessel.

FIGS. 3-5 are flattened views of alternative electrode support designs.

FIG. 6A is a perspective view of a multi-turn spiral electrode support having three spiral turns.

FIG. 6B is a perspective view of a multi-turn spiral electrode support having two spiral turns. The electrode support is shown extending from a catheter.

FIG. 7 is a perspective view of a single revolution electrode support extending from a catheter.

FIGS. 8A and 8B are perspective views of a double spiral electrode array.

FIG. 8C shows a double spiral electrode array similar to that of FIG. 8A extending from a catheter.

DETAILED DESCRIPTION

Figure 9A:
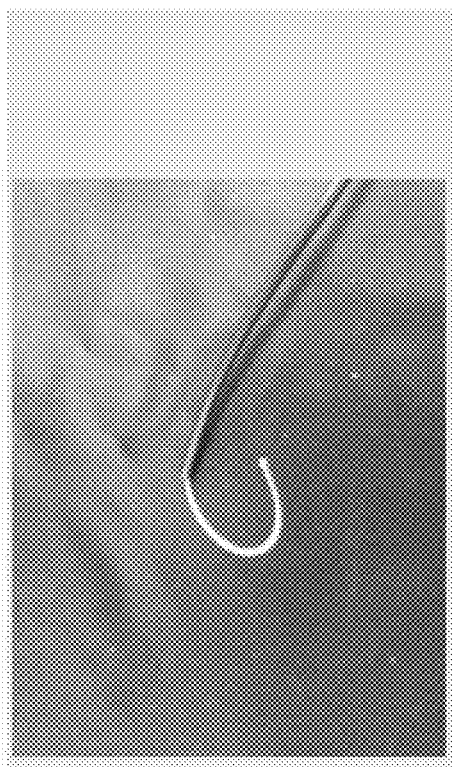
FIGS. 9A through 9D are a sequence of perspective views showing deployment of a single revolution electrode support being deployed from a catheter.

This application describes intravascular electrode carrying members used to support neuromodulation electrodes within a blood vessel. For convenience this description focuses on the use of the described electrodes in a system in which both parasympathetic and sympathetic nerve fibers are independently targeted using electrodes on a single electrode carrying member positioned in the SVC. However, the disclosed concepts are equally suitable for use in other vessels, and also during therapy during which electrodes on the electrode carrying member deliver electrical therapy to only a single type of nerve fiber.

The illustrated electrode carrying members are designed to bias arrays of multiple electrodes in contact with the surrounding vascular wall—such that when energy from a neuromodulation system energizes the electrodes, target nerve fibers outside the blood vessel are captured. The embodiments are designed to position the electrodes in positions suitable for delivering electrical therapy to the target fibers from the intended position of the array within the vasculature. Some embodiments give the user (or automated mapping feature of a neuromodulation system) a variety of electrodes to select between when choosing the optimal electrode or electrode combination to deliver the intended therapy.

Referring to FIG. 1, a first electrode carrying member 10 includes an elongate electrode support 12 extending from a shaft that extends from the distal end of a catheter 14. When viewed as flattened as shown in FIG. 1, the longitudinal axis of the electrode support 12 extends angularly from the longitudinal axis of the catheter 14. The electrode support 12 is biased to firm a spiral shape as shown in FIG. 2A, so that it extends at least partially circumferentially around the interior wall of the blood vessel as shown in FIG. 2B. The outer diameter of the spiral, in the absence of forces compressing or contracting the spiral, is greater than the diameter of the target blood vessel, such that the electrode support 12 is radially outwardly biased against the vessel wall. The geometry, dimensions, spiral pitch, etc of the electrode carrying member as well as the arrangement of electrodes on the electrode carrying member are selected such that when the electrode carrying member is positioned in the target location within the blood vessel, electrodes on the electrode carrying member are in suitable positions for the intended therapy.

Multiple spaced-apart electrodes 13 are disposed on the electrode support 12, facing radially outwardly. FIG. 1 shows eight electrodes, although more (e.g. up to 32) or fewer could be used. The spacing of electrodes may be selected to be between approximately 1-8 mm, with a preferred spacing of approximately 5 mm.

The electrode support may be a ribbon or strip formed using a planar, flexible, substrate. The substrate may be polyimide, polyurethane, polyethylene, silicone rubber, fluoropolymer, stainless steel, platinum-iridium, MP35N, titanium and other biocompatible metals/polymers/elastomers. In some embodiments, the electrode support is a flex circuit.

The electrodes are disposed at one face of the substrate—the face that opposes the vessel wall when the system is implanted—such that the active electrode surfaces are in contact with the vessel wall and the substrate provides an electrically insulative backing and electrically isolates the electrodes from one another. The electrodes may be deposited or printed onto the substrate, or they may be positioned in or molded into the substrate or openings formed through the substrate. Conductors or conductive traces (not shown) are formed, deposited, printed on or molded into/onto the substrate.

FIG. 1 shows shape elements 16 (shown using dashed lines) embedded within or positioned on the electrode support 12. The shape elements bias the electrode support in its intended shape. They may be pre-biased elements or shape memory elements. Exemplary materials include nitinol, stainless steel, shape memory polymers, or other materials. Note that in lieu of the shape elements, the electrode support itself may be formed of biased or shape-memory material.

Note with reference to FIG. 2B that the dimensions of the electrode support 12 need not position electrodes around the full circumference of the target blood vessel. That figure shows the electrode support element 12 positioned to capture target sympathetic and parasympathetic fibers from within the SVC. As disclosed in International Application No. PCT/US2012/046329, entitled System and Method for Neuromodulation, heart rate can be lowered and blood pressure elevated or sustained by capturing sympathetic and parasympathetic fibers using electrodes positioned against the posterior wall of the SVC. Thus for that procedure, the electrode support 12 is proportioned to place electrodes at least within (and, in some designs, only within) an electrode coverage zone extending at least from a postero-lateral position in the SVC to at least a postero-medial position. As can be seen in FIGS. 1A and 1B, because the electrode support is shape-biased towards the vessel wall, the catheter body is also biased against the wall of the vessel. Also, by manufacturing the electrode supports using thin substrate materials, obstruction of blood flow is minimized or avoided.

During use, the electrode support is compressed within a deployment catheter that is advanced to a target site within the target blood vessel. The electrode support expands within the blood vessel as the deployment catheter is withdrawn from the electrode support.

The FIG. 3 embodiment is similar to the FIG. 1 embodiment, but the electrode support includes a pair of strips or ribbons supporting the electrodes. Other embodiments might have additional strips, with suitable embodiments having between 1 and 8 such strips. The strips/ribbons may have equal or different number of electrodes. This arrangement allows the electrode support member to carry a larger number of electrodes, giving a great selection of electrode combinations (including combinations involving electrodes from each strip) for use in delivering energy to the target nerve fibers. The two strips can be parallel within each other shown—so as to, or they might be non-parallel. FIG. 5 illustrates an electrode support 12c using three non-parallel strips. The orientations and bias of the strips are selected to provide electrode combinations for stimulus that are most suitable for the positions of the target nerve fibers relative to the electrode position within the blood vessel. In the "fork" arrangement of FIG. 5, the strips might be biased to spiral in the same direction (i.e. clockwise or counterclockwise) around the vessel wall, or in opposite directions. As another alternative, the outer strips might be biased to spiral, while the center strip does not spiral but instead extends longitudinally away from the catheter body.

FIG. 4 shows that the electrode support 12d need not be a strip or ribbon, but can have a greater longitudinal dimension than the strips of the other embodiments. This shape can give room for a larger multi-electrode array, such as the multi-column multi-row array illustrated in FIG. 4. Biasing elements 16 in the FIG. 4 electrode support cause the support to curl or spiral into a tubular shape within the blood vessel.

The spiral electrode supports may be made of other materials besides planar substrates, including but not limited to elongate shafts, strands or tubes, including those made from materials commonly used for intravascular or cardiac leads used chronically or acutely within the body. FIGS. 6A through 8B illustrate electrode supports made of such alternate materials, although the designs shown in FIGS. 6A through 8B might be constructed using substrate materials disclosed in connection with FIGS. 1-5.

FIGS. 6A and 6B illustrates spiral electrode supports 112a and 112b biased such that when released from a deployment catheter 200 they assumes a multi-turn spiral configuration. The FIG. 7 embodiment is similar, but provides a spiral with fewer than two revolutions.

In the FIG. 8A-8C embodiment, the electrode support 112c includes a pair of spiral members (similar to FIG. 3 described above) extending from a common shaft. As with the other embodiments, the shafts supporting the electrode supports are preferably laterally offset from the longitudinal axis of the spiral, such that when the electrode support is deployed, its supporting shaft is offset from the longitudinal axis of the vessel (preferably against the vessel wall).

Figure 9B:
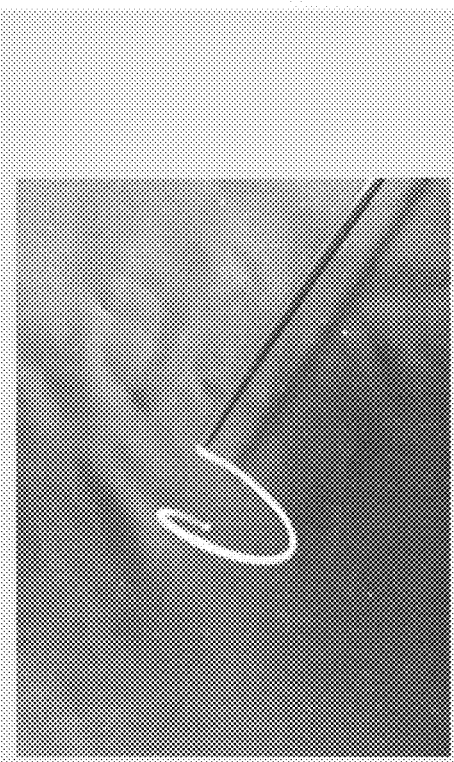
Figure 9C:
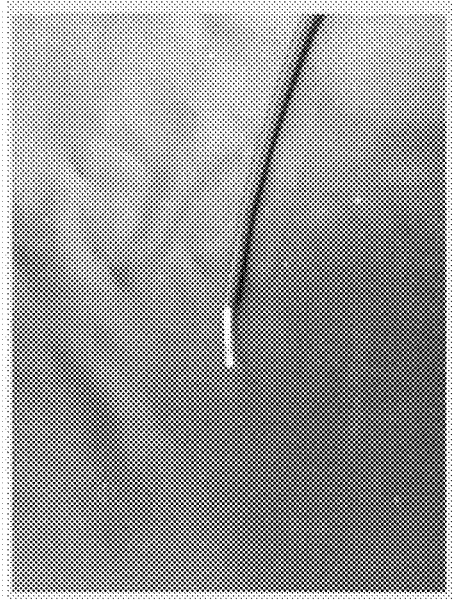
Figure 9D:
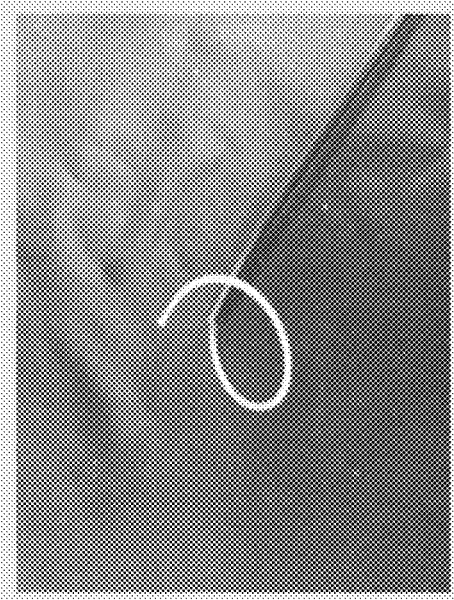

The sequence of FIG. 9A-9D illustrates a distal portion of a spiral electrode support being advanced from the distal end of the deployment catheter 200, and illustrates how the electrode support assumes its biased spiral configuration as it leaves the distal end of the catheter.

What is claimed is:

1. A neuromodulation catheter positionable in a blood vessel having a wall, comprising:
    a catheter body having a longitudinal axis;
    an electrically insulative substrate comprising a pair of elongate fingers carried at a distal end of the catheter body, the substrate having a first face and a second face on an opposite side of the substrate from the first face, wherein each finger extends non-parallel to the other finger and is biased to form a spiral configuration with the first face facing outwardly and the second face facing inwardly;

a plurality of electrodes spaced apart on the first face of each finger.

2. The neuromodulation catheter of claim 1, wherein, a first one of the fingers is biased to spiral in a clockwise direction and a second one of the fingers is biased to spiral in a counterclockwise direction.

3. The neuromodulation catheter of claim 2, further including a third finger between the first and second fingers, wherein the third finger is non-parallel to the first and second fingers and includes a plurality of spaced apart electrodes on the first face thereof.

4. The neuromodulation catheter of claim 3, wherein the third finger is biased to extend generally longitudinally from the catheter body.

5. The neuromodulation catheter of claim 1, further including a plurality of shape elements embedded within or positioned on the substrate, the shape elements biasing each of the fingers to form the spiral configuration.

6. The neuromodulation catheter of claim 5, wherein the finger includes at least two edges, and wherein the shape members extend along said at least two edges of the substrate.

* * * * *